(12) United States Patent
Drysen

(10) Patent No.: US 7,274,957 B2
(45) Date of Patent: *Sep. 25, 2007

(54) MULTIFUNCTIONAL CATHETER HANDLE

(75) Inventor: Darrell Drysen, La Puente, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/322,582

(22) Filed: Dec. 30, 2005

(65) Prior Publication Data

US 2006/0106297 A1    May 18, 2006

Related U.S. Application Data

(63) Continuation of application No. 10/386,594, filed on Mar. 12, 2003, now Pat. No. 6,987,995.

(51) Int. Cl.
*A61B 5/04* (2006.01)
(52) U.S. Cl. ............. 600/374; 600/381; 600/585; 604/95.04; 604/528
(58) Field of Classification Search ............. 600/374, 600/381, 585; 604/95.01, 95.04, 523, 528
See application file for complete search history.

(56) References Cited

U.S. PATENT DOCUMENTS 6,468,260 B1 * 10/2002 Bumbalough et al. ...... 604/523
6,795,721 B2 * 9/2004 Coleman et al. ............ 600/374
6,987,995 B2 * 1/2006 Drysen ....................... 600/374
2003/0125663 A1 * 7/2003 Coleman et al. ......... 604/95.04

FOREIGN PATENT DOCUMENTS

EP     1038545 A2    9/2000

OTHER PUBLICATIONS

European Search Report dated Mar. 11, 2005 for European Patent Application No. 04251416.6.

* cited by examiner

*Primary Examiner*—Lee S. Cohen
(74) *Attorney, Agent, or Firm*—Christie, Parker & Hale, LLP.

(57) ABSTRACT

The invention is directed to a multifunctional catheter handle. The handle comprises a handle body and a core mounted within the handle body. A piston is provided having a distal end mounted in the handle body and a proximal end extending outside the handle body, to which a catheter body can be attached. The piston is longitudinally moveable relative to the core and handle body. A first puller wire anchor is fixedly mounted to the core. A cam receiver is mounted in the handle body so that the cam receiver is longitudinally slidable relative to the piston and core. A second puller wire anchor is fixedly mounted to the cam receiver. A generally cylindrical cam is mounted distal to the cam receiver in surrounding relation to the piston and core. Rotation of the cam relative to the piston and core causes longitudinal movement of the cam receiver and second puller wire anchor.

25 Claims, 11 Drawing Sheets

MULTIFUNCTIONAL CATHETER HANDLE

CROSS-REFERENCE TO RELATED APPLICATION(S)

This application is a continuation of U.S. application Ser. No. 10/386,594, now U.S. Pat. No. 6,987,995, entitled MULTIFUNCTIONAL CATHETER HANDLE, filed Mar. 12, 2003, the entire contents of which is incorporated herein by reference.

BACKGROUND OF THE INVENTION

Electrode catheters have been in common use in medical practice for many years. They are used to stimulate and map electrical activity in the heart and to ablate sites of aberrant electrical activity.

In use, the electrode catheter is inserted into a major vein or artery, e.g., femoral artery, and then guided into the chamber of the heart which is of concern. Within the heart, the ability to control the exact position and orientation of the catheter tip is critical and largely determines how useful the catheter is.

Steerable catheters are generally well-known. For example, U.S. Pat. No. Re 34,502 describes a catheter having a control handle comprising a housing having a piston chamber at its distal end. A piston is mounted in the piston chamber and is afforded lengthwise movement. The proximal end of the elongated catheter body is attached to the piston. A puller wire is attached to the housing and extends through the piston, through the catheter body, and into a tip section at the distal end of the catheter body. The distal end of the puller wire is anchored in the tip section of the catheter. In this arrangement, lengthwise movement of the piston relative to the housing results in deflection of the catheter tip section.

The design described in RE 34,502 is generally limited to a catheter having a single puller wire. If a multifunctional catheter is desired, such as a catheter that can be deflected to form two different curves (e.g., deflect in more than one direction), more than one puller wire becomes necessary. The handle design disclosed in RE 34,502 is not suitable for a two puller wire system. Accordingly, a need exists for a control handle capable of independently moving each of two puller wires.

SUMMARY OF THE INVENTION

The present invention is directed to a multifunctional catheter handle. In one embodiment, the handle comprises a handle body and a core mounted within the handle body. A piston is provided having a distal end mounted in the handle body and a proximal end extending outside the handle body, to which a catheter body can be attached. The piston is longitudinally moveable relative to the core and handle body. A first puller wire anchor is fixedly mounted to the core. A cam receiver is mounted in the handle body so that the cam receiver is longitudinally slidable relative to the piston and core. A second puller wire anchor is fixedly mounted to the cam receiver. A generally cylindrical cam is mounted distal to the cam receiver in surrounding relation to the piston. Rotation of the cam relative to the piston causes longitudinal movement of the cam receiver and second puller wire anchor.

In another embodiment, the invention is directed to a multifunctional catheter handle comprising a handle body and a core mounted within the handle body. The core has a longitudinal passage extending therethrough. A piston has a distal end mounted in the handle body in surrounding relation to the core and a proximal end extending outside the handle body. The piston is longitudinally moveable relative to the core and handle body. A first puller wire anchor is fixedly mounted to the core. A generally tubular cam receiver is provided having proximal and distal ends. The generally tubular cam receiver is mounted in surrounding relation to the piston so that the cam receiver is longitudinally slidable over the piston. A second puller wire anchor is fixedly mounted to the cam receiver. A generally cylindrical cam is mounted distal to the cam receiver in surrounding relation to the piston and core. The cam has a ramped proximal end. Rotation of the cam relative to the piston and core causes longitudinal movement of the cam receiver and second puller wire anchor.

In another embodiment, the invention is directed to a catheter comprising an elongated catheter body having proximal and distal ends. A first puller wire extends through the catheter body. The distal end of the first puller wire is anchored at or near the distal end of the catheter body or to a structure mounted at the distal end of the catheter body. A second puller wire extends through the catheter body and has a distal end anchored at or near the distal end of the catheter body or to a structure mounted at the distal end of the catheter body. A control handle is mounted at the proximal end of the catheter body. The control handle comprises a handle body and a core mounted within the handle body. The core has a longitudinal passage extending therethrough. A piston is provided having a distal end mounted in the handle body and a proximal end extending outside the handle body. The proximal end of the catheter is mounted, directly or indirectly, to the piston. The piston is longitudinally moveable relative to the core and handle body. A cam receiver is mounted in the handle body so that the cam receiver is longitudinally slidable relative to the piston and core. A generally cylindrical cam is mounted distal to the cam receiver in surrounding relation to the piston. Rotation of the cam relative to the piston causes longitudinal movement of the cam receiver and second puller wire anchor. The first puller wire is fixedly mounted to the core such that longitudinal movement of the piston and catheter body relative to the core causes longitudinal movement of the first puller wire relative to the catheter body. The second puller wire is anchored to the cam receiver such that rotation of the cam causes longitudinal movement of the cam receiver and second puller wire relative to the piston and catheter body.

BRIEF DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

Figure 1:
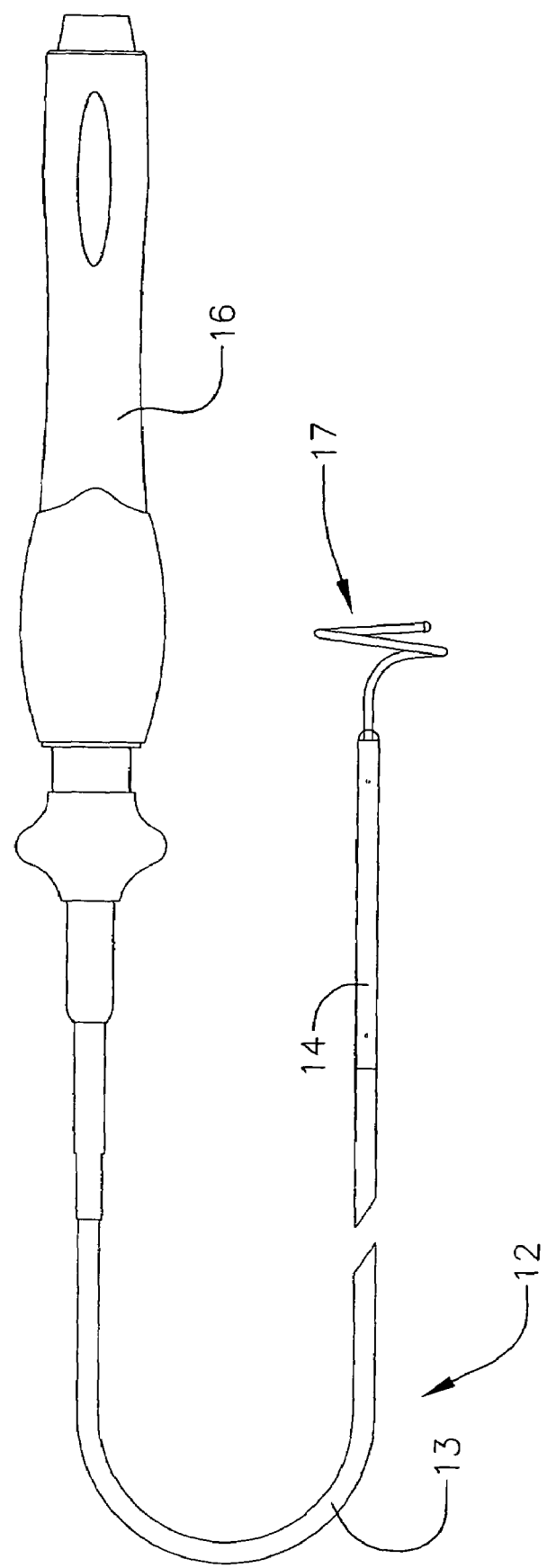
FIG. 1 is a side view of an embodiment of the catheter of the invention.

According to the invention, there is provided a catheter having a mapping assembly at its distal end. As shown in FIG. 1, the catheter comprises an elongated catheter body 12 having proximal and distal ends, a control handle 16 at the proximal end of the catheter body, and a mapping assembly 17 mounted at the distal end of the catheter body.

Figure 2:
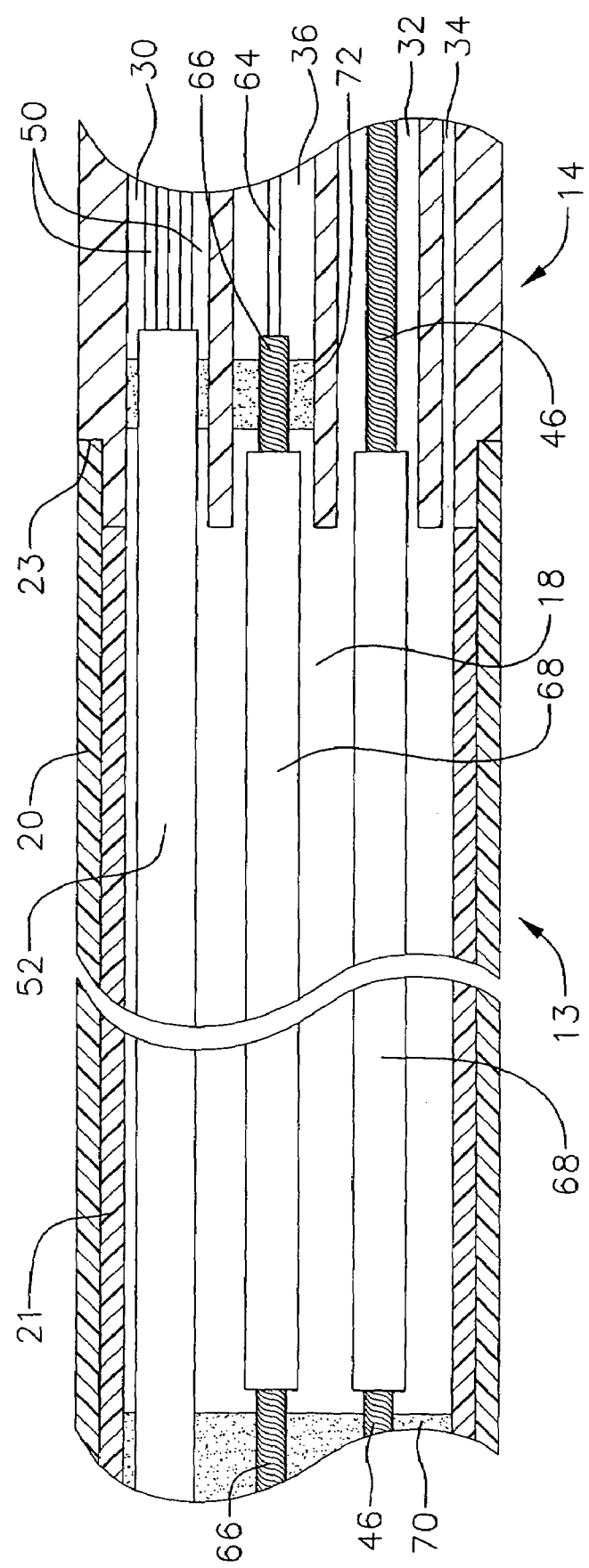
FIG. 2 is a schematic side cross-sectional view of the catheter body of FIG. 1, including the junction between the catheter body and distal shaft.

In the depicted embodiment, the catheter body 12 includes an elongated proximal shaft 13 at its proximal end and a shorter distal shaft 14 at its distal end. With reference to FIG. 2, the proximal shaft 13 comprises an elongated tubular construction having a single, axial or central lumen 18. The proximal shaft 13 is flexible, i.e., bendable, but substantially non-compressible along its length. The proximal shaft 13 can be of any suitable construction and made of any suitable material. A presently preferred construction comprises an outer wall 20 made of polyurethane or PEBAX. The outer wall 20 comprises an imbedded braided mesh of stainless steel or the like, as is generally known in the art, to increase torsional stiffness of the proximal shaft 13 so that, when the control handle 16 is rotated, the distal shaft 14 will rotate in a corresponding manner.

The outer diameter of the proximal shaft 13 is not critical, but is preferably no more than about 8 French, more preferably 7 French. Likewise the thickness of the outer wall 20 is not critical, but is thin enough so that the central lumen 18 can accommodate any desired wires, cables and/or tubes. The inner surface of the outer wall 20 is lined with a stiffening tube 21 to provide improved torsional stability. The outer diameter of the stiffening tube 21 is about the same as or slightly smaller than the inner diameter of the outer wall 20. The stiffening tube 21 can be made of any suitable material, such as polyimide, which provides very good stiffness and does not soften at body temperature.

The distal shaft 14 comprises a short section of tubing having four lumens, namely, a lead wire lumen 30, a contraction wire lumen 32, a support member lumen 34, and a deflection wire lumen 36. The tubing of the distal shaft 14 is made of a suitable non-toxic material that is preferably more flexible than the proximal shaft 13. A presently preferred material for the distal shaft tubing is braided polyurethane, i.e., polyurethane with an embedded mesh of braided stainless steel or the like. The size of each lumen is not critical, but is sufficient to house the components extending therethrough, as discussed further below.

The useful length of the catheter, i.e., that portion that can be inserted into the body excluding the mapping assembly 17, can vary as desired. Preferably the useful length ranges from about 110 cm to about 120 cm. The length of the distal shaft 14 is a relatively small portion of the useful length, and preferably ranges from about 3.5 cm to about 10 cm, more preferably from about 5 cm to about 6.5 cm.

A preferred means for attaching the proximal shaft 13 to the distal shaft 14 is illustrated in FIG. 2. The proximal end of the distal shaft 14 comprises an outer circumferential notch 23 that receives the inner surface of the outer wall 20 of the catheter body 12. The distal shaft 14 and catheter body 12 are attached by glue or the like. If desired, a spacer (not shown) can be provided within the proximal shaft 13 between the distal end of the stiffening tube 20 and the proximal end of the distal shaft 14 to provide a transition in flexibility at the junction of the proximal shaft and distal shaft, which allows the junction of the proximal and distal shafts to bend smoothly without folding or kinking. An example of such a spacer is described in more detail in U.S. Pat. No. 5,964,757, the disclosure of which is incorporated herein by reference.

At the distal end of the distal shaft 14 is a mapping assembly 17, as shown in FIGS. 3 to 6. The mapping assembly 17 comprises a generally straight proximal region 38 and a generally circular main region 39. The proximal region 38 is mounted on the distal shaft 14, as described in more detail below, so that its axis is generally parallel to the axis of the distal shaft. The proximal region 38 preferably has an exposed length, e.g., not contained within the distal shaft 14, ranging from about 3 mm to about 12 mm, more preferably about 3 mm to about 8 mm, still more preferably about 5 mm inch, but can vary as desired.

Figure 3:
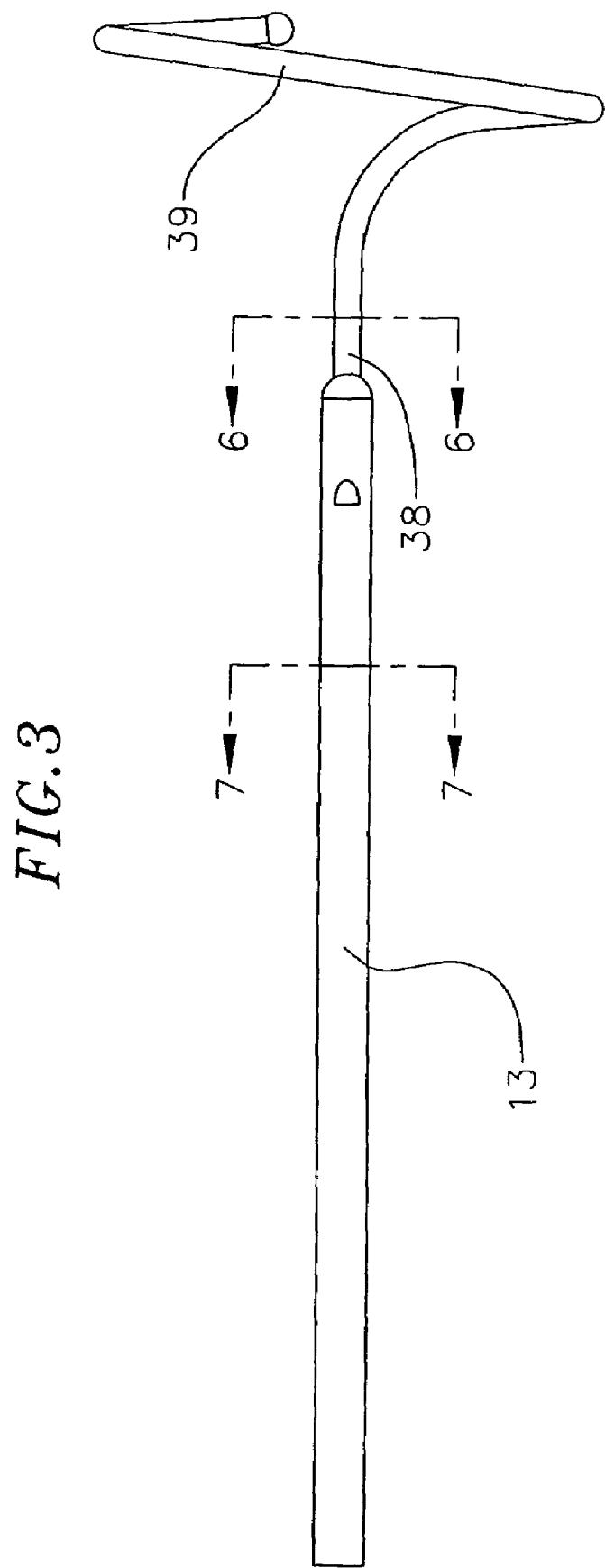
FIG. 3 is a side view of the distal shaft and mapping assembly of the catheter according to FIG. 1.

The generally circular main region 39 is generally traverse to the catheter body 12. The generally circular main region 39 is preferably generally perpendicular to the catheter body 12. The generally circular main region 39 can form a flat circle or can be very slightly helical, as shown in FIG. 3. The main region 39 has an outer diameter preferably ranging to about 10 mm to about 25 mm, more preferably about 12 mm to about 20 mm. The generally circular main region 39 can curve in a clockwise direction or a counterclockwise direction. The mapping assembly 17 is formed of a non-conductive cover 22, which is preferably generally tubular, but can have any cross-sectional shape as desired. The non-conductive cover 22 can be made of any suitable material, and is preferably made of a biocompatible plastic such as polyurethane or PEBAX. The non-conductive cover 22 can be pre-formed into the desired generally circular shape of the generally circular main region. Alternatively, the shape of the generally circular main region can be defined by a wire or other component extending through the non-conductive cover 22.

In the depicted embodiment, a pre-formed support member 24 extends through the non-conductive cover 22 to define the shape of the generally circular main region 39. The support member 24 is made of a material having shape-memory, i.e., that can be straightened or bent out of its original shape upon exertion of a force and is capable of substantially returning to its original shape upon removal of the force. A particularly preferred material for the support member 24 is a nickel/titanium alloy. Such alloys typically comprise about 55% nickel and 45% titanium, but may comprise from about 54% to about 57% nickel with the balance being titanium. A preferred nickel/titanium alloy is Nitinol, which has excellent shape memory, together with ductility, strength, corrosion resistance, electrical resistivity and temperature stability.

Figure 4A:
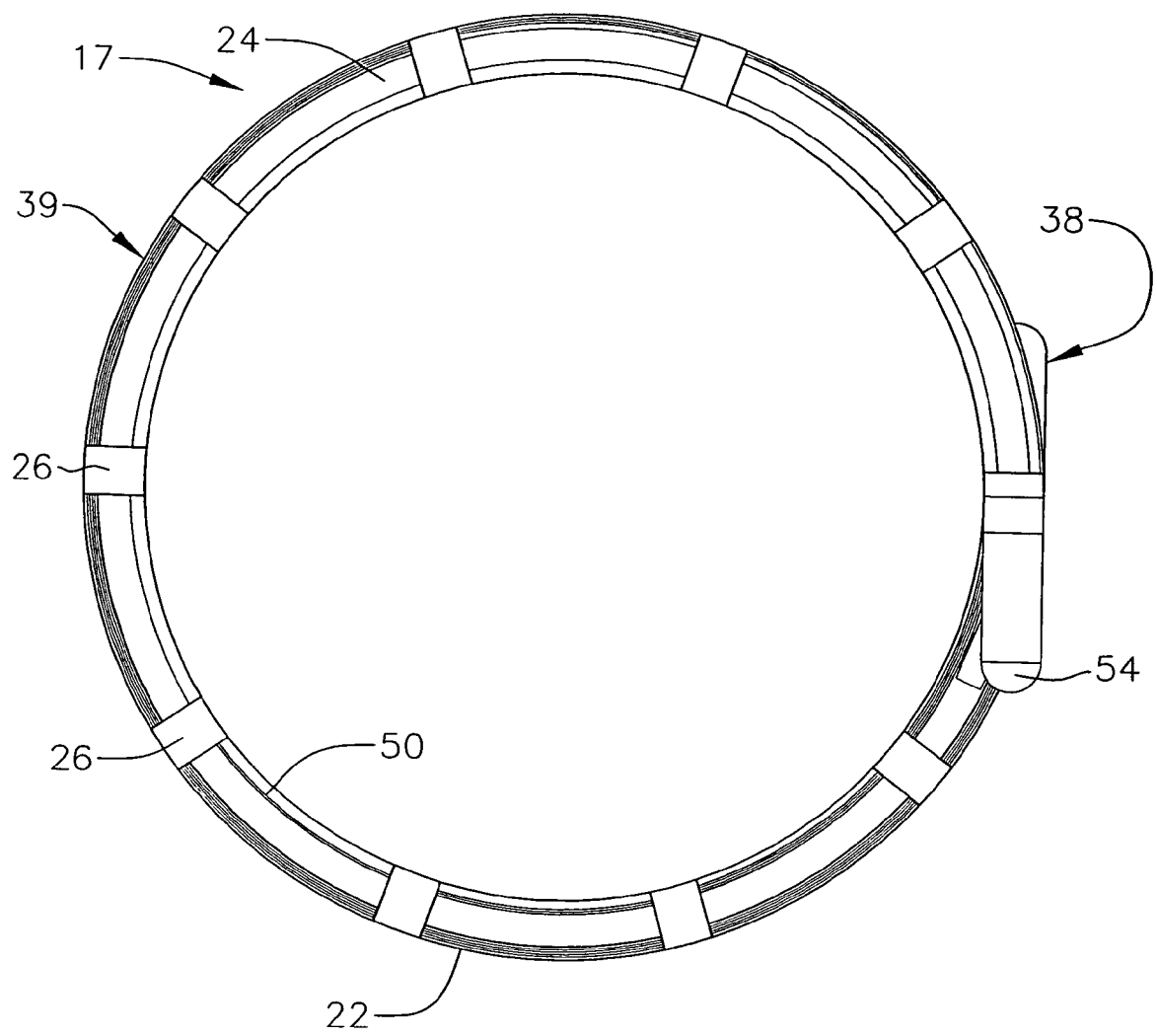
FIG. 4a is schematic view of the mapping assembly showing one arrangement of the ring electrodes.
Figure 4B:
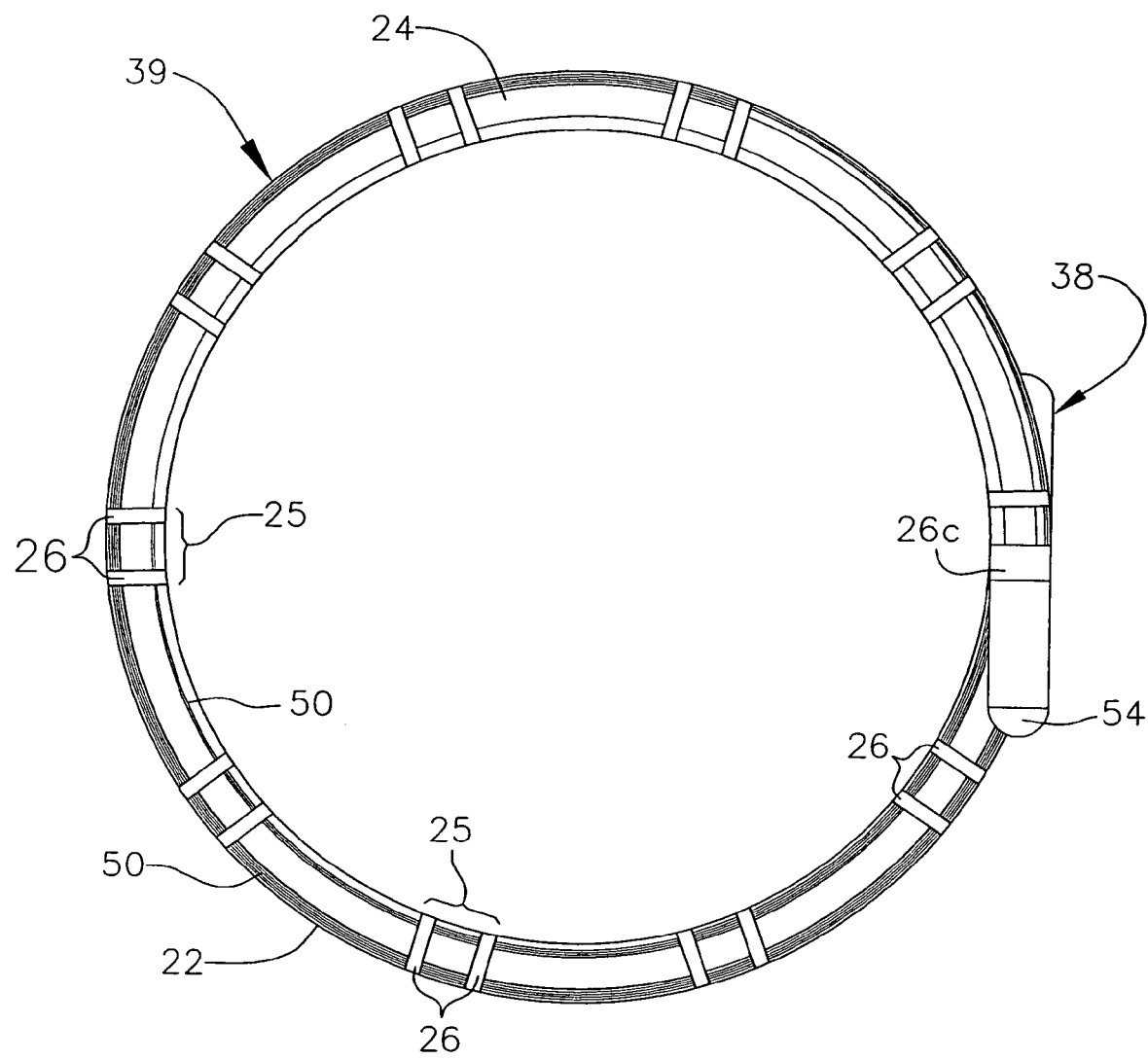
FIG. 4b is schematic view of the mapping assembly showing an alternative arrangement of the ring electrodes.

A series of ring electrodes 26 are mounted on the non-conductive cover 22 of the generally circular main region 39 of the mapping assembly 17, as shown in FIGS. 4a and 4b. The ring electrodes 26 can be made of any suitable solid conductive material, such as platinum or gold, preferably a combination of platinum and iridium, and mounted onto the non-conductive cover 22 with glue or the like. Alternatively, the ring electrodes 26 can be formed by coating the non-conductive cover 22 with an electrically conducting material, like platinum, gold and/or iridium. The coating can be applied using sputtering, ion beam deposition or an equivalent technique.

In a preferred embodiment, each ring electrode 26 is mounted by first forming a hole in the non-conductive cover 22. An electrode lead wire 50 is fed through the hole, and the ring electrode 26 is welded in place over the lead wire and non-conductive cover 22. The lead wires 50 extend through the non-conductive cover 22 and into the catheter body 12. The proximal end of each lead wire 50 is electrically connected to a suitable connector (not shown), which is connected an appropriate monitor or other device for receiving and displaying the information received from the ring electrodes 26.

The number of ring electrodes 26 on the assembly can vary as desired. Preferably the number of ring electrodes ranges from about six to about twenty, more preferably from about eight to about twelve. In one embodiment, the assembly carries ten ring electrodes. The ring electrodes 26 can be approximately evenly spaced around the generally circular main region 39, as shown in FIG. 4a. In a particularly preferred embodiment, a distance of approximately 5 mm is provided between the centers of the ring electrodes 26.

An alternative electrode arrangement is depicted in FIG. 4b. In this embodiment, the mapping assembly 17 includes a series of ring electrode pairs 25. Each ring electrode pair 25 comprises two closely-spaced ring electrodes 26. As used herein, the term "ring electrode pair" refers to a pair of ring electrodes that are arranged closer to each other than they are to the other adjacent ring electrodes. Preferably the distance between two electrodes 26 of an electrode pair 25 is less than about 3 mm, more preferably less than about 2 mm, still more preferably from about 0.5 mm to about 1.5 mm. The number of electrode pairs 25 can vary as desired, and preferably ranges from 6 to 14 pairs, more preferably 10 pairs.

In a particularly preferred embodiment, the mapping assembly carries 10 pairs of electrodes with a space of approximately 1 mm between the two electrodes 26 of each pair 25. Preferably each ring electrode 26 is relatively short, having a length ranging from about 0.4 mm to about 0.75 mm, with the most distal ring electrode 26c being longer than the other ring electrodes, preferably having a length ranging from about 1 mm to about 1.5 mm. The longer ring electrode provides a signal to the user when the catheter is being viewed under fluoroscopy. Specifically, because the mapping assembly is generally circular, it can be difficult for the user to determine which electrodes are placed at a particular location in the heart. By having one ring electrode, such as the most distal ring electrode, sized differently from the other ring electrodes, the user has a reference point when viewing the catheter under fluoroscopy.

Regardless of the size and number of the ring electrodes 26, the electrode pairs 25 are preferably approximately evenly spaced around the generally circular main region 39. The closely-spaced electrode pairs 25 allow for more accurate detection of near field pulmonary vein potential versus far field atrial signals, which is very important when trying to treat atrial fibrillation. Specifically, the near field pulmonary vein potentials are very small signals whereas the atria, located very close to the pulmonary vein, provides much larger signals. Accordingly, even when the mapping array is placed in the pulmonary vein, it can be difficult for the physician to determine whether the signal is a small, close potential (from the pulmonary vein) or a larger, farther potential (from the atria). Closely-spaced bipoles permit the physician to more accurately determine whether he is looking at a close signal or a far signal. Accordingly, by having closely-spaced electrodes, one is able to target exactly the locations of myocardial tissue that have pulmonary vein potentials and therefore allows the clinician to deliver therapy to the specific tissue. Moreover, the closely-spaced electrodes allow the physician to determine the exact anatomical location of the ostium by the electrical signal.

If desired, additional electrodes (not shown) could be mounted along the distal shaft 14 and/or the generally straight proximal section 39.

Figure 5:
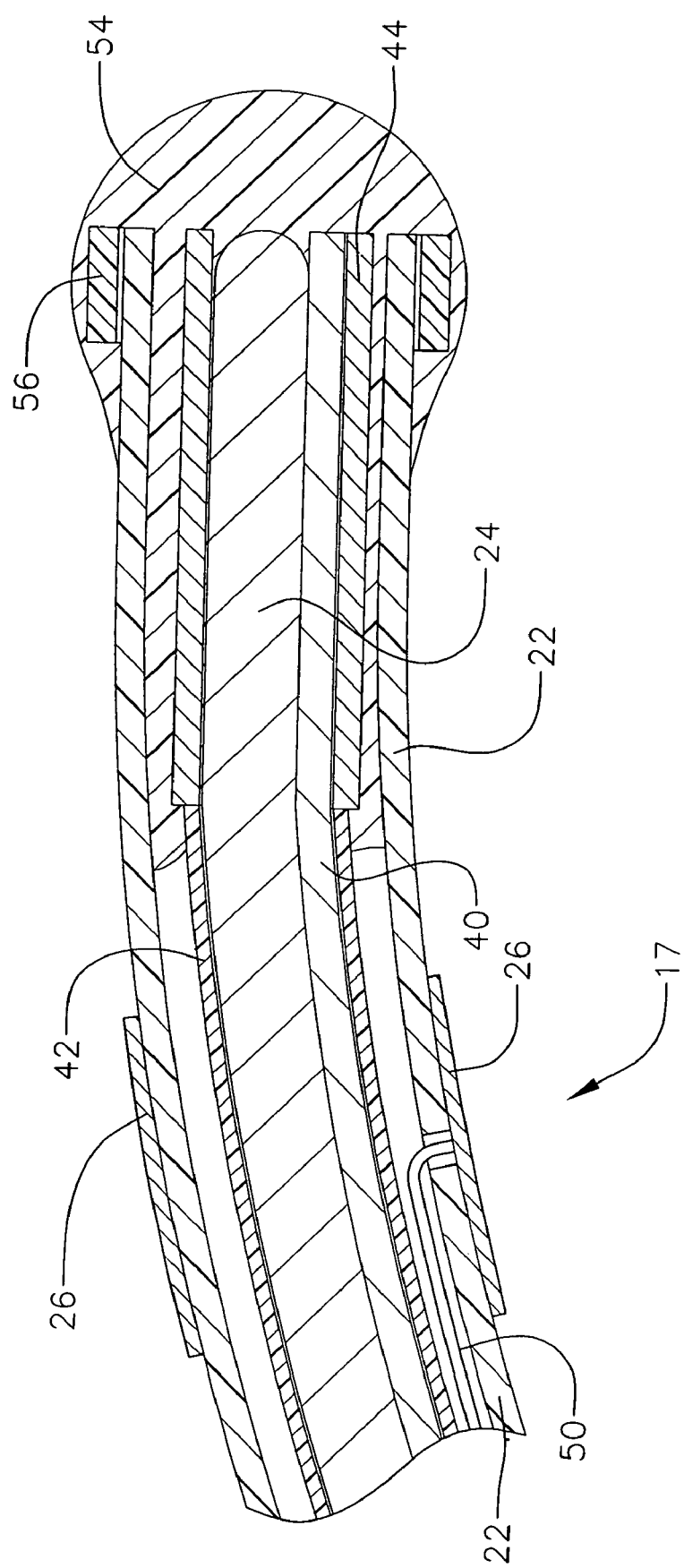
FIG. 5 is a side cross-sectional view of the distal end of the mapping assembly of the catheter of FIG. 1.
Figure 6:
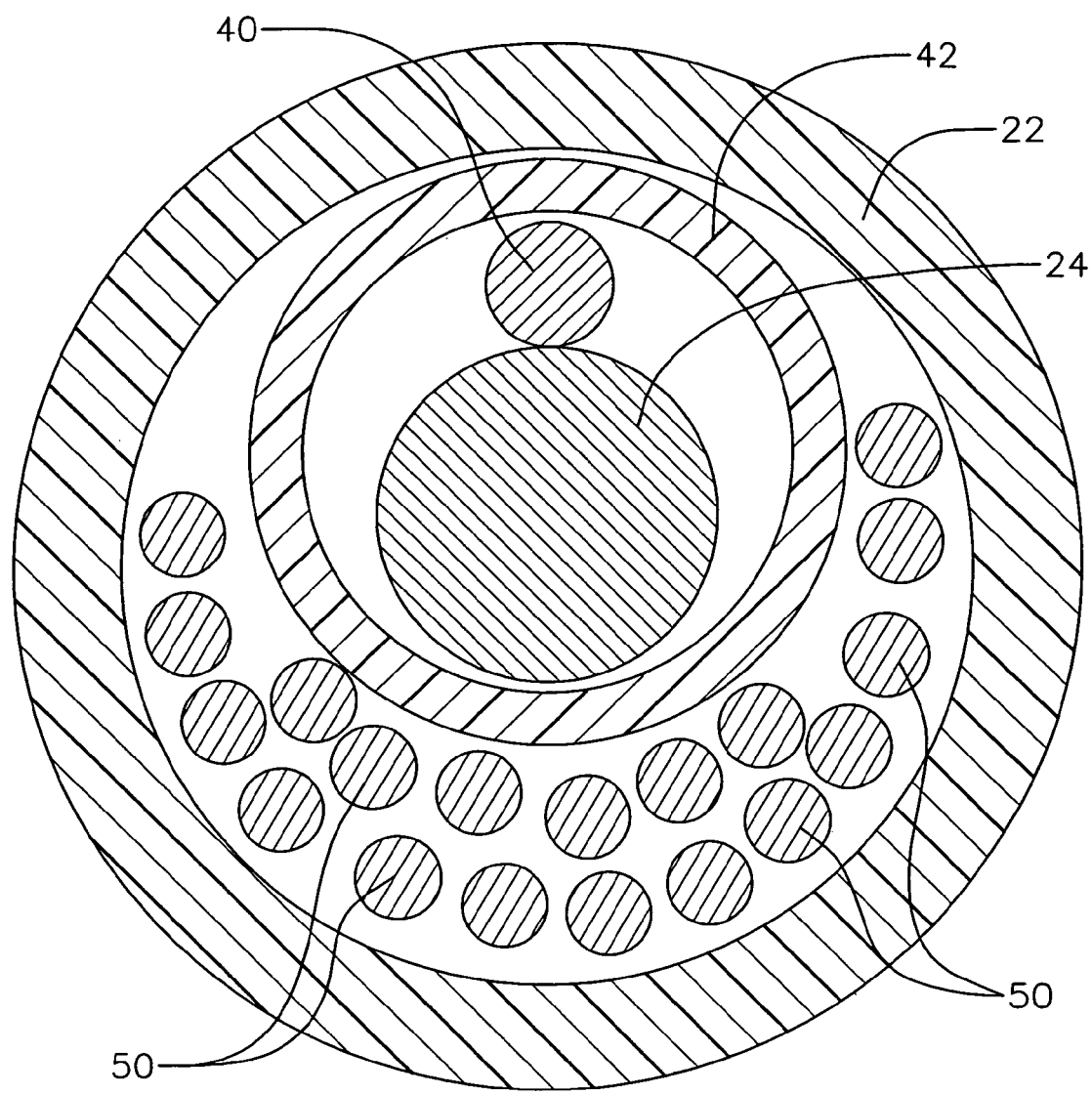
FIG. 6 is an end cross-sectional view of the mapping assembly of the catheter of FIG. 3 along line 6-6.
Figure 7:
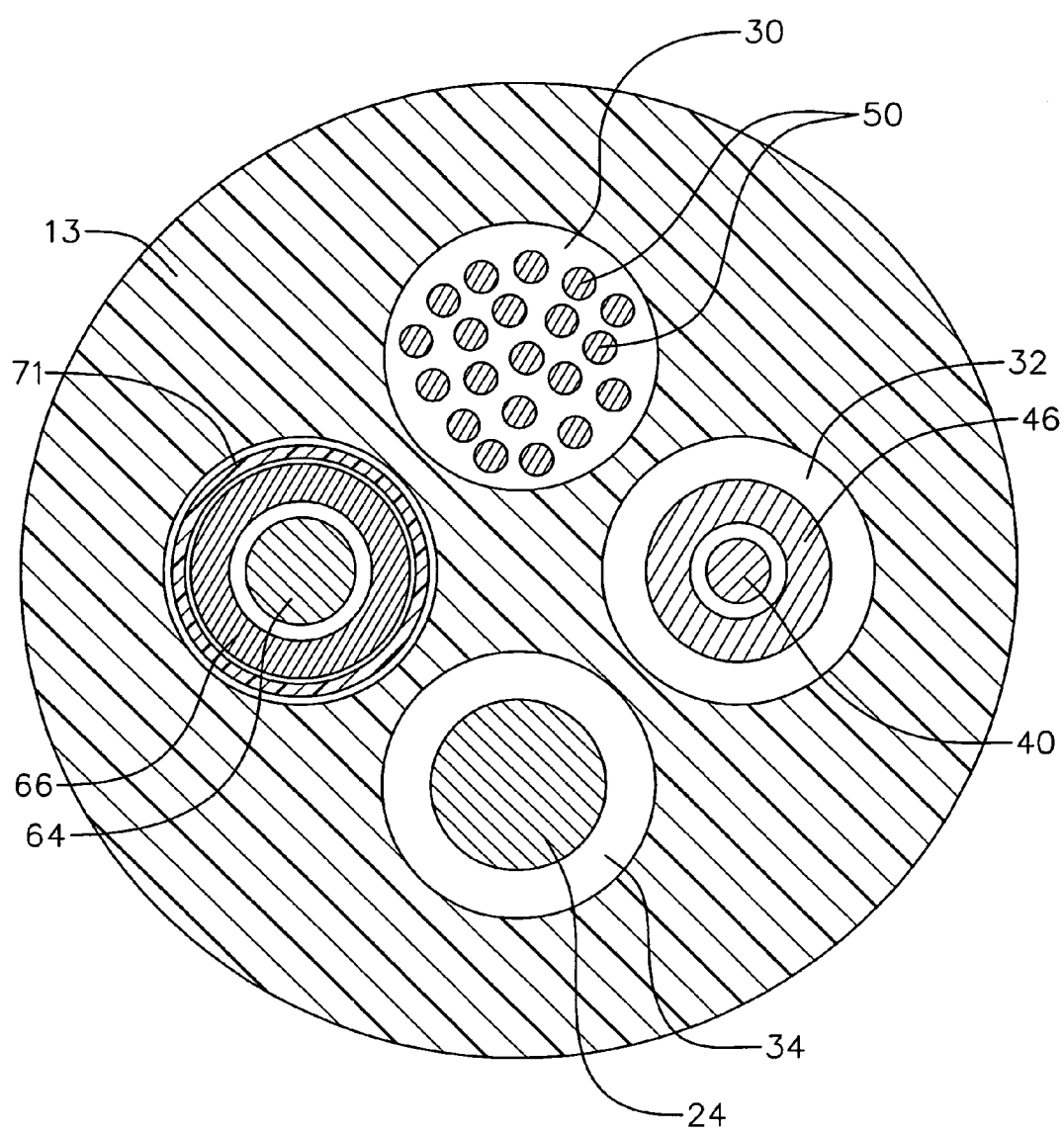
FIG. 7 is an end cross-sectional view of the distal shaft of the catheter of FIG. 3 along line 7-7.

A contraction wire 40 is provided to contract the generally circular main region 39 to thereby reduce its diameter. The contraction wire 40 has a proximal end anchored in the control handle 16, which is used to manipulate the contraction wire as described further below. The contraction wire 40 extends through the central lumen 18 of the proximal shaft 13, through the contraction wire lumen 32 of the distal shaft 14 and into the non-conductive cover 22. The portion of the contraction wire 40 extending through the non-conductive cover 22 is positioned on the side of the generally circular main region 39 closer to the center of the generally circular main region, as best shown in FIGS. 5 and 6. The center of the generally circular main region refers to the center of the circle formed by the generally circular main region. With this arrangement, contraction of the generally circular main region 39 is dramatically improved over arrangements where the position of the contraction wire 40 is not so controlled.

As shown in FIGS. 5 and 6, within the mapping assembly 17, the contraction wire 40 extends through a plastic tube 42. In one embodiment, the plastic tube 42 comprise three layers, including an inner layer of polyimide over which a braided layer is formed, the braided layer comprising a braided stainless steel mesh or the like, as is generally known in the art. The braided layer enhances the strength of the plastic tube 42, reducing the tendency for contraction wire 40 to straighten the preformed curve of the mapping assembly. A thin plastic layer of polytetrafluoroethylene is provided over the braided layer to protect the braided layer from getting tangled with the lead wires 50 within the non-conductive cover 22. The plastic tube 42 has a proximal end anchored to the distal end of the distal shaft 14. The support member 24 extends through the plastic tube 42 with the contraction wire 40. The distal ends of the support member 24 and the contraction wire 40 are soldered or otherwise attached to a small stainless steel tube 44. With this arrangement, the relative positions of the contraction wire 40 and the support member 24 can be controlled so that the contraction wire 40 can be positioned on the side of the generally circular region closer to the center of the generally circular region, as described above. The contraction wire 40 on the inside of the curve pulls the support member 24 to the inside of the curve, enhancing contraction of the generally circular region 39. Further, when the plastic tube 42 includes a braided layer, it keeps the contraction wire 40 from tearing through the non-conductive cover 22.

A first compression coil 46 is situated within the proximal shaft 13 and distal shaft 14 in surrounding relation to the contraction wire 40. The first compression coil 46 extends from the proximal end of the proximal shaft 13 and through the contraction wire lumen 32. The first compression coil 46 is made of any suitable metal, preferably stainless steel, and is tightly wound on itself to provide flexibility, i.e., bending, but to resist compression. The inner diameter of the first compression coil 46 is preferably slightly larger than the diameter of the contraction wire 40. The outer surface of the first compression coil 46 is covered by a flexible, non-conductive sheath 68, e.g., made of polyimide tubing. The first compression coil 46 preferably is formed of a wire having a square or rectangular cross-sectional area, which makes it less compressible than a compression coil formed from a wire having a circular cross-sectional area. As a result, the first compression coil 46 keeps the catheter body 12, and particularly the distal shaft 14, from deflecting when the contraction wire 40 is manipulated to contract the mapping assembly 17 as it absorbs more of the compression.

The first compression coil 46 is anchored at its proximal end to the outer wall 20 of the catheter body 12 by proximal glue joint 70 and to the distal shaft 14 by distal glue joint 72. Both glue joints 70 and 72 preferably comprise polyurethane glue or the like. The glue may be applied by means of a syringe or the like through a hole made between the outer surface of the catheter body 12 and the central lumen 18. Such a hole may be formed, for example, by a needle or the like that punctures the outer wall 20 of the catheter body 12 which is heated sufficiently to form a permanent hole. The glue is then introduced through the hole to the outer surface of the first compression coil 46 and wicks around the outer circumference to form a glue joint about the entire circumference of the compression coil. In the depicted embodiment, the distal end of the mapping assembly 17 is sealed closed with a dome 54 of polyurethane glue or the like. A short ring 56, made of metal or plastic, and preferably polyamide, is mounted within the distal end of the non-conductive cover 22. The short ring 56 prevents the distal end of the non-conductive cover 22 from collapsing, thereby maintaining the diameter of the non-conductive cover at its distal end.

At the junction of the distal shaft 14 and the mapping assembly 17, the non-conductive cover 22 is attached to the distal shaft by glue or the like. The plastic tube 42 has its proximal end inserted and glued in the distal end of the distal shaft 14. The glue from the plastic tube 42 can further serve to anchor the distal end of the first compression coil 46 in place within the contraction wire lumen 32. The support member 24 extends from the support member lumen 32 into the plastic tube 42 within the non-conductive cover 22. The proximal end of the support member 24 terminates a short distance within the support member lumen 34, approximately about 5 mm, so as not to adversely affect the ability of the distal shaft 14 to deflect. However, if desired, the proximal end of the support member 24 can extend further into the catheter body 12.

The lead wires 50 attached to the ring electrodes 26 extend through the lead wire lumen 30 of the distal shaft 14, through the central lumen 18 of the catheter body 12, and the control handle 16, and terminate at their proximal end in a connector (not shown). The portion of the lead wires 50 extending through the central lumen 18 of the catheter body 12, control handle 16 and proximal end of the distal shaft 14 are enclosed within a protective sheath 52, which can be made of any suitable material, preferably polyimide. The protective sheath 52 is anchored at its distal end to the proximal end of the distal shaft 14 by gluing it in the lead wire lumen 30 with polyurethane glue or the like.

A deflection wire 64 is provided for deflection of the distal shaft 14. The deflection wire 64 extends through the proximal shaft 13, and is anchored at its proximal end to control handle 16 and at its distal end to the distal shaft 14. The deflection wire 64 is made of any suitable metal, such as stainless steel or Nitinol, and is preferably coated with Teflon® or the like. The coating imparts lubricity to the puller wire 64. The puller wire 64 preferably has a diameter ranging from about 0.006 to about 0.010 inch.

The deflection wire 64 extends into the deflection wire lumen 36 of the distal shaft 14. Preferably the deflection wire 64 is anchored at its distal end to the sidewall of the distal shaft 14, as is generally described in U.S. Pat. No. 6,371,955, the disclosure of which is incorporated herein by reference.

A second compression coil 66 is situated within the proximal shaft 13 in surrounding relation to the deflection wire 64. The second compression coil 66 extends from the proximal end of the proximal shaft 13 to the distal end of the proximal shaft. The second compression coil 66 is made of any suitable metal, preferably stainless steel, and is tightly wound on itself to provide flexibility, i.e., bending, but to resist compression. The inner diameter of the second compression coil 66 is preferably slightly larger than the diameter of the deflection wire 64. The Teflon® coating on the deflection wire 64 allows it to slide freely within the second compression coil 66. Within the proximal shaft 13, the outer surface of the second compression coil 66 is also covered by a flexible, non-conductive sheath 68, e.g., made of polyimide tubing. The second compression coil 66 is anchored at its proximal end to the outer wall 20 of the catheter body 12 by the proximal glue joint 70 and to the distal shaft 14 by the distal glue joint 72. Within the deflection wire lumen 36 of the distal shaft 14, the deflection wire 64 and second compression coil 66 extends through a plastic, preferably Teflon®, puller wire sheath 71, which prevents the puller wire 64 from cutting into the wall of the distal shaft when the distal shaft is deflected.

Longitudinal movement of the contraction wire 40 relative to the catheter body 12, which results in contraction of the generally circular main region 39 of the mapping assembly 17, is accomplished by suitable manipulation of the control handle 16. Similarly, longitudinal movement of the deflection wire 64 relative to the catheter body 12, which results in deflection of the distal shaft 14, is accomplished by suitable manipulation of the control handle 16. Suitable control handles for manipulating more than one wire are described, for example, in U.S. Pat. Nos. 6,468,260, 6,500, 167, and 6,522,933, the disclosures of which are incorporated herein by reference.

Figure 8:
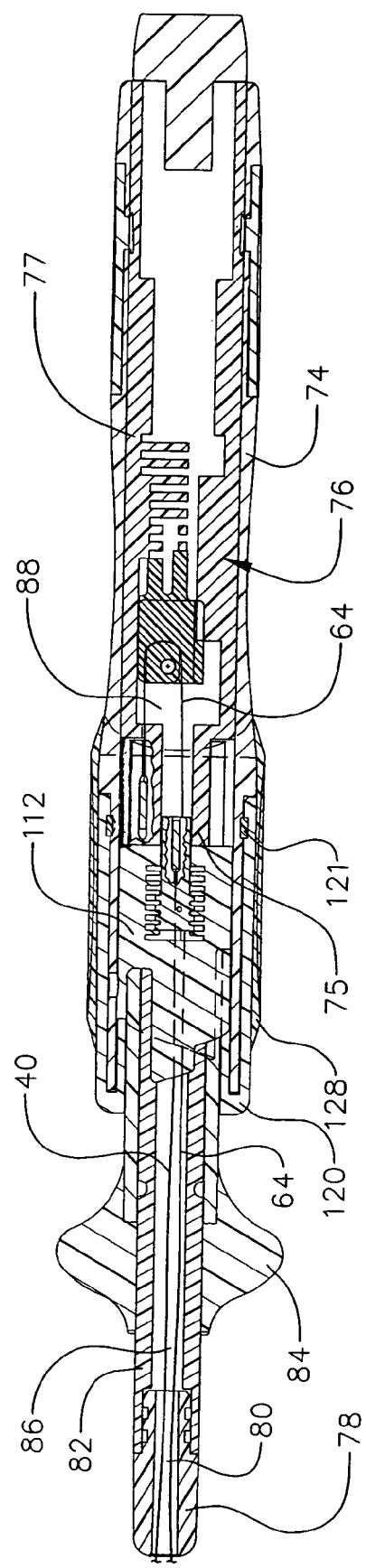
FIG. 8 is a side cross-sectional view of a control handle in accordance with the invention.
Figure 9:
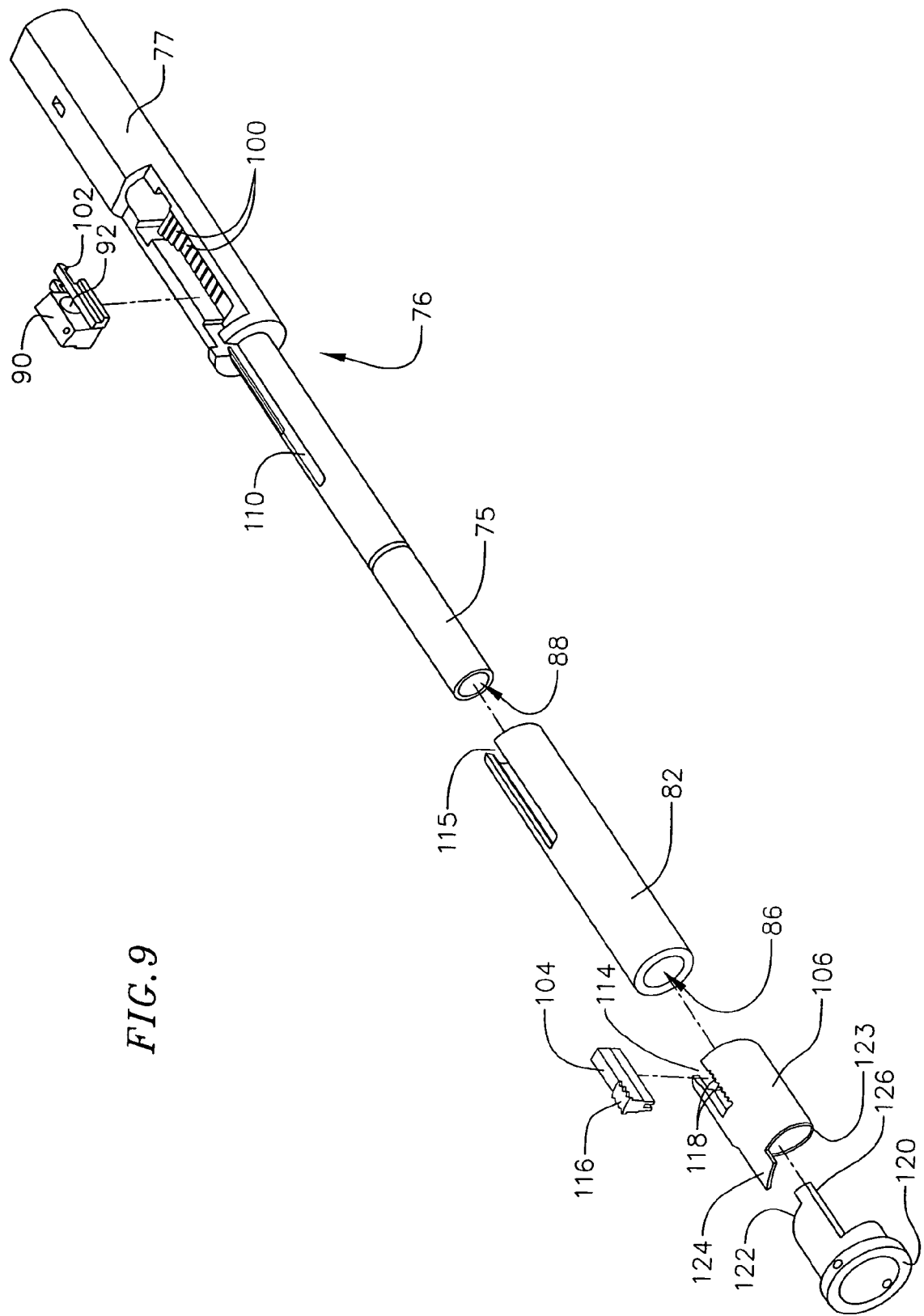
FIG. 9 is an exploded perspective view of the interior components of the control handle shown in FIG. 8.
Figure 10:
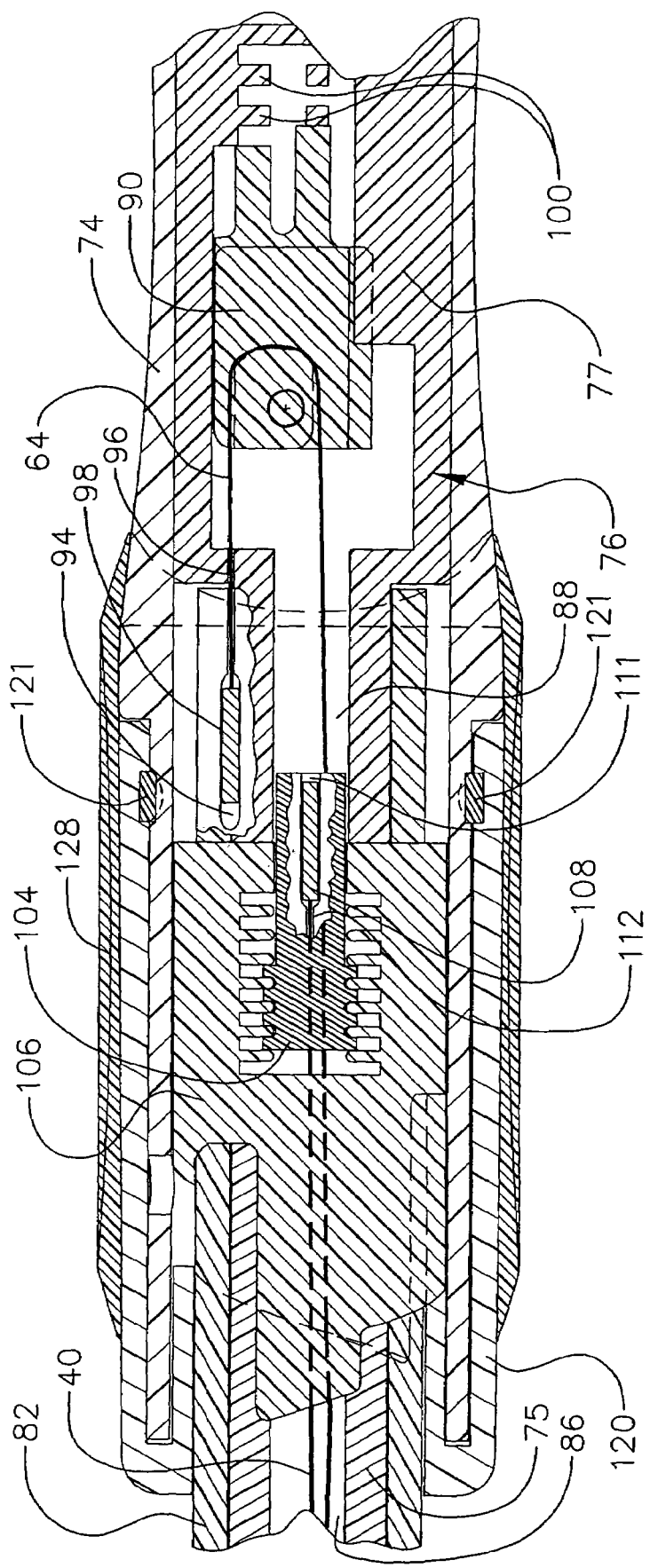
FIG. 10 is an enlarged side cross-sectional view of the control handle of FIG. 8 showing the deflection wire adjuster and the contraction wire adjuster.

In one embodiment, the catheter includes a control handle 16 as shown in FIGS. 8 to 10. The control handle 16 includes a handle body 74 in which a core 76 is fixedly mounted. Although in the depicted embodiment, the core 76 is separate from the handle body 74, the core could instead be formed as a single unitary piece with the handle body. The core has a generally cylindrical distal region 75 and a generally cylindrical proximal region 77 having a larger diameter than the distal region. For longitudinal movement of the deflection wire 64, a piston 82 is slidably mounted over the distal region 77 of the core 76. The proximal end of the piston 82 is maintained within the handle body 74, and the distal end of the piston extends outside the handle body. A thumb knob 84 is mounted in surrounding relation to a portion of the distal end of the piston 82 so that the user can more easily move the piston longitudinally relative to the core 76 and handle body 74. The proximal end of the catheter body 12 is fixedly mounted to the distal end of the piston 82 through a tip portion 78 that is mounted on the distal end of the piston. The proximal end of the catheter body 12 is inserted into an axial passage 86 in communication with the axial passage 80 of the tip portion 78, and the core 76 includes an axial passage 88 in communication with the axial passage in the piston.

The lead wires 50, contraction wire 46 and deflection wire 66 that extend through the catheter body 12 extend out the proximal end of the catheter body and through the axial passages in the tip portion 78, piston 82 and core 76. The lead wires 50 can extend out the proximal end of the control handle 16 or can be connected to a connector (not shown) that is incorporated into the control handle, as is generally known in the art.

The proximal end of the deflection wire 64 is anchored to the core 76. As best seen in FIG. 10, the portion of the axial passage 88 extending through the proximal region 77 of the core 76 has a larger diameter than the portion of the axial passage extending through the distal region 75 of the core 76. A deflection wire adjuster 90 is adjustably mounted, as described further below, in a portion of the axial passage 88 near the distal end of the proximal region 77 of the core 76. The deflection wire adjuster 90 has an opening 92 extending therethrough in a direction generally transverse, and preferably generally perpendicular, to the axial passage 88 of the core 76. The deflection wire 64 extends through the opening 92 in the deflection wire adjuster 90 such that the deflection wire changes directions.

The distal region 77 of the core 76 includes a generally rectangular opening 94 that extends generally parallel to the axial passage 88 of the core. A channel 96 connects the proximal end of the generally rectangular opening 94 to the distal end of the portion of the axial passage 88 in the proximal region 75 of the core 76. The proximal end of the deflection wire 64 extends through the channel 96 and into the generally rectangular opening 94. A deflection wire anchor 98, which can comprise a short piece of hypodermic stock, is fixedly attached, for example, by crimping, to a portion of the proximal end of the deflection wire 64 within the generally rectangular opening 94. The deflection wire anchor 98 has a diameter greater than the width of the channel 96 and thus prevents the proximal end of the deflection wire 64 from being pulled through the channel, thereby anchoring the deflection wire to the core 76. Thus, the deflection wire anchor 98 is fixedly mounted to the core 76 even though the deflection wire anchor still has a small amount of free play within the opening 94.

In use, the piston 82 is moved distally relative to the handle body 74 and core 76, thereby pulling the catheter body 12 distally relative to the deflection wire 64, which is anchored to the core. As a result, the deflection wire 64 pulls on the side of the distal shaft 14 to which it is anchored, thereby deflecting the distal shaft in that direction. To straighten the distal shaft 14, the piston 82 is moved proximally back to its original position relative to the handle body 74 and core 76.

Manipulation of the deflection wire adjuster 90 adjusts the amount of free play in the deflection wire 64. As noted above, the deflection wire adjuster 90 is adjustably mounted in a portion of the axial passage 88 near the distal end of the proximal region 77 of the core 76. The portion of the axial passage 88 in which the deflection wire adjuster 90 is mounted includes a series of ridges 100 extending along the surface of the core 76, with the ridges being generally perpendicular to the axis of the core. The deflection wire adjuster 90 carries an outwardly extending tab 102 that fits in the spaces between the ridges 100. The deflection wire adjuster 90 can be moved along the length of the core 76 and snapped into place by placing the tab 102 between two ridges 100. As the deflection wire adjuster 90 is moved proximally (away from catheter body 12) less free play is provided for the deflection wire 64. The precise mechanism for adjusting the amount of free play of the deflection wire 64 is not critical, and alternative mechanisms can be provided. Alternatively, the deflection wire 64 can be anchored directly to the core 76 so that it is not adjustable.

The control handle 16 is also used for longitudinal movement of the contraction wire 40. The contraction wire 40 extends from the catheter body 12, through the axial passage 86 in the piston 82 and through the axial passage 88 within the distal region 75 of the core 76. The proximal end of the contraction wire 40 is anchored to a contraction wire adjuster 104 that is slidably mounted in the core 76.

The contraction wire adjuster 104 is generally rectangular having a bottom region 108 that extends downward through a slot 110 in the proximal region 77 of the core 76, the slot being in communication with the axial passage 88 of the core. The proximal end of the contraction wire 40, which, as noted above, extends through the axial passage 88, is anchored in the contraction wire adjuster 104 in a manner very similar to the manner in which the deflection wire 64 is anchored to the core 76, as described above. Specifically, a contraction wire anchor 108, which can comprise a short piece of hypodermic stock, is fixedly attached, for example, by crimping, to a portion of the proximal end of the contraction wire 40 within an opening 110 in the contraction wire adjuster 104. A channel 112 connects the opening 110 to the axial passage 88 in the core. The contraction wire anchor 98 has a diameter greater than the width of the channel 112 and thus prevents the proximal end of the contraction wire 40 from being pulled through the channel, thereby anchoring the contraction wire to the contraction wire adjuster 104.

The distal end of the contraction wire adjuster 104 is adjustably attached to a cam receiver 106. The cam receiver 106 is generally tubular, having a short slot 114 extending from its proximal end sized to receive the distal end of the contraction wire adjuster 104. The cam receiver 106 is slidably mounted over the piston 82 and the distal region 75 of the core 76 with the bottom portion of the contraction wire adjuster 104 positioned in the slot 114 in the core and a corresponding slot 115 in the piston. Thus, the contraction wire anchor 98 is fixedly mounted to the cam receiver 106 through the contraction wire adjuster 104, even though the contraction wire anchor has some free play within the opening 110 in the contraction wire adjuster.

As shown in FIG. 9, the top of the distal end of the contraction wire adjuster 104 includes a series of outwardly extending teeth 116 that mate with a plurality of notches 118 within the slot 114 of the cam receiver 106 so that the contraction wire adjuster can be snapped into the cam receiver. The position of the contraction wire adjuster 104 relative to the cam receiver 106 can be longitudinally adjusted by repositioning the teeth 116 relative to the notches 118, to thereby adjust the tension on the contraction wire 40. Alternatively, the contraction wire 40 is not adjustable, in which case the contraction wire anchor 98 is mounted within an opening (not shown) within the cam receiver 106.

Longitudinal movement of the cam receiver 106 and contraction wire adjuster 104 relative to the core 76, to which the catheter body 12 is indirectly mounted, results in longitudinal movement of the contraction wire 40 relative to the catheter body. Longitudinal movement of the cam receiver 106 is accomplished through a cam 120 mounted in the control handle 16 in surrounding relation to the piston 82 and distal region 75 of the core 76. A retaining ring 121 maintains the longitudinal position of the cam 120 relative to the handle body 74.

The cam 120 includes a ramped proximal surface 122. The cam receiver 106 includes a ramped distal surface 123 and an outwardly extending tab 124 at the most distal point of the ramped distal surface. The tab 124 contacts the ramped proximal surface 122 of the cam 120. When the cam 120 is rotated counterclockwise, the ramped proximal surface 112 correspondingly rotates and pushes the cam receiver 104 proximally relative to the core 76 and catheter body 12. As the cam receiver 104 and the attached contraction wire adjuster 104 are moved proximally relative to the core 76 and catheter body 12, the contraction wire 40 is pulled proximally to thereby contract the generally circular main region 39 of the mapping assembly 17.

The ramped proximal surface 122 of the cam 120 includes an outwardly extending tab 126 at its most proximal point. As the cam 120 is rotated counterclockwise, the tab 124 on the cam receiver 104 contacts the tab 126 on the ramped proximal surface 122, thereby prohibiting further rotation of the cam relative to the cam receiver. As the cam 120 is rotated clockwise, the tab 126 on the ramped proximal surface 122 pushes the tab 124 on the cam receiver 104 such that the cam receiver moves distally, thereby releasing the tension on the contraction wire 40 so that the generally circular main region 39 of the mapping assembly 17 returns to its original configuration. As would be recognized by one skilled in the art, the direction of the ramped proximal surface 122 can be changed so that clockwise rotation of the cam 120 causes contraction of generally circular main region 39 of the mapping assembly 17 and counterclockwise rotation causes it to return to its original configuration. A flexible grip 128 is provided over the cam 120 for the user to more easily and comfortably rotate the cam 120.

In use, a suitable guiding sheath is inserted into the patient with its distal end positioned at a desired mapping location. An example of a suitable guiding sheath for use in connection with the present invention is the Preface™ Braiding Guiding Sheath, commercially available from Biosense Webster, Inc. (Diamond Bar, Calif.). The distal end of the sheath is guided into one of the atria. A catheter in accordance with the present invention is fed through the guiding sheath until its distal end extends out of the distal end of the guiding sheath. As the catheter is fed through the guiding sheath, the mapping assembly 17 is straightened to fit through the sheath. Once the distal end of the catheter is positioned at the desired mapping location, the guiding sheath is pulled proximally, allowing the deflectable distal shaft 14 and mapping assembly 17 to extend outside the sheath, and the mapping assembly 17 returns to its original shape due to the shape-memory of the support member 24. The mapping assembly 17 is then inserted into a pulmonary vein or other tubular region (such as the coronary sinus, superior vena cava, or inferior vena cava) so that the outer circumference of the generally circular main region 39 of the assembly is in contact with a circumference inside the tubular region. Preferably at least about 50%, more preferably at least about 70%, and still more preferably at least about 80% of the circumference of the generally circular main region is in contact with a circumference inside the tubular region.

The circular arrangement of the electrodes 26 permits measurement of the electrical activity at that circumference of the tubular structure so that ectopic beats between the electrodes can be identified. The size of the generally circular main region 39 permits measurement of electrical activity along a diameter of a pulmonary vein or other tubular structure of or near the heart because the circular main region has a diameter generally corresponding to that of a pulmonary vein or the coronary sinus.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A multifunctional handle comprising:
a handle body;
a core mounted within the handle body, the core having a longitudinal passage extending therethrough;
a piston having a proximal end mounted in the handle body and a distal end extending outside the handle body, the piston being longitudinally moveable relative to the core and handle body;
a tip portion mounted on the distal end of the piston, the tip portion including a first axial passage, wherein the piston includes a second axial passage in communication with the first axial passage in the tip portion, and wherein the longitudinal passage in the core is in communication with the second axial passage in the piston;
a first puller wire anchor fixedly mounted to the core;
a cam receiver mounted within the handle body so that the cam receiver is longitudinally slidable relative to the piston and core;
a second puller wire anchor fixedly mounted to the cam receiver; and
a generally cylindrical cam mounted distal to the cam receiver in surrounding relation to the piston, wherein rotation of the cam relative to the piston causes longitudinal movement of the cam receiver and second puller wire anchor.

2. A multifunctional handle according to claim 1, wherein the cam has a ramped proximal end.

3. A multifunctional handle according to claim 2, wherein the cam receiver is generally tubular and is mounted in surrounding relation to the core.

4. A multifunctional handle according to claim 3, wherein the cam receiver has a distal end with a tab extending distally therefrom, wherein the tab contacts the ramped proximal end of the cam.

5. A multifunctional handle according to claim 4, wherein the ramped proximal end of the cam has a tab extending proximally therefrom, such that, when the cam is rotated relative to the piston and core, the tab on the cam contacts the tab on the cam receiver to thereby limit the ability of the cam to rotate.

6. A multifunctional handle according to claim 1, wherein the second puller wire anchor is fixedly mounted to the cam receiver by being fixedly mounted within a puller wire adjuster that is adjustably mounted to the cam receiver such that the longitudinal position of the puller wire adjuster relative to the cam can be altered.

7. A multifunctional handle according to claim 6, wherein the puller wire adjuster has one or more teeth extending outward therefrom in a direction generally perpendicular to the axis of the handle and is mounted within a slot in the cam receiver, the slot containing one or more notches that mate with the teeth.

8. A multifunctional handle according to claim 1, further comprising a puller wire adjuster mounted within the longitudinal passage in the core at a position proximal to the first puller wire anchor, wherein the longitudinal position of the puller wire adjuster relative to the core can be altered, the puller wire adjuster comprising an opening extending therethrough in a direction generally transverse to the axis of the handle, such that a wire extending through the core and having an end anchored to the first puller wire anchor can pass through the opening of the puller wire adjuster and reverse directions.

9. A multifunctional handle comprising:
   a handle body;
   a core mounted within the handle body, the core having a longitudinal passage extending therethrough;
   a piston having a proximal end mounted in the handle body in surrounding relation to the core and a distal end extending outside the handle body, the piston being longitudinally moveable relative to the core and handle body;
   a thumb control mounted in surrounding relation to a portion of the distal end of the piston;
   a first puller wire anchor fixedly mounted to the core;
   a generally tubular cam receiver having proximal and distal ends and being mounted in surrounding relation to the piston so that the cam receiver is longitudinally slidable over the piston;
   a second puller wire anchor fixedly mounted to the cam receiver; and
   a generally cylindrical cam mounted distal to the cam receiver in surrounding relation to the piston and core and having a ramped proximal end, wherein rotation of the cam relative to the piston and core causes longitudinal movement of the cam receiver and second puller wire anchor.

10. A multifunctional handle according to claim 9, wherein the cam receiver has a tab extending distally therefrom that contacts the ramped proximal end of the cam.

11. A multifunctional handle according to claim 10, wherein the ramped proximal end of the cam has a tab extending proximally therefrom, such that, when the cam is rotated relative to the piston and core, the tab on the cam contacts the tab on the cam receiver to thereby limit the ability of the cam to rotate.

12. A multifunctional handle according to claim 9, wherein the second puller wire anchor is fixedly mounted to the cam receiver by being fixedly mounted within a puller wire adjuster that is adjustably mounted to the cam receiver such that the longitudinal position of the puller wire adjuster relative to the cam can be altered.

13. A multifunctional handle according to claim 12, wherein the puller wire adjuster has one or more teeth extending outward therefrom in a direction generally perpendicular to the axis of the handle and is mounted within a slot in the cam receiver, the slot containing one or more notches that mate with the teeth.

14. A multifunctional handle according to claim 9, further comprising a puller wire adjuster mounted within the core at a position proximal to the first puller wire anchor, wherein the longitudinal position of the puller wire adjuster relative to the core can be altered, the puller wire adjuster comprising an opening extending therethrough in a direction generally transverse to the axis of the handle, such that a wire extending through the core and having an end anchored to the first puller wire anchor can pass through the opening of the puller wire adjuster and reverse directions.

15. A catheter comprising:
   an elongated catheter body having proximal and distal ends;
   a first puller wire extending through the catheter body and having proximal and distal ends, wherein the distal end of the first puller wire is anchored at or near the distal end of the catheter body or to a structure mounted at the distal end of the catheter body;
   a second puller wire extending through the catheter body and having proximal and distal ends, wherein the distal end of the second puller wire is anchored at or near the distal end of the catheter body or to a structure mounted at the distal end of the catheter body;
   a control handle at the proximal end of the catheter body, the control handle comprising:
      a handle body;
      a core mounted within the handle body, the core having a longitudinal passage extending therethrough;
      a piston having a proximal end mounted in the handle body and a distal end extending outside the handle body, wherein the proximal end of the catheter is mounted to the piston, the piston being longitudinally moveable relative to the core and handle body;
      a tip portion mounted on the distal end of the piston, wherein the proximal end of the catheter body is mounted on the tip portion;
      a cam receiver mounted within the handle body so that the cam receiver is longitudinally slidable relative to the piston and core; and
      a generally cylindrical cam mounted distal to the cam receiver in surrounding relation to the piston, wherein rotation of the cam relative to the piston causes longitudinal movement of the cam receiver and second puller wire anchor;
   wherein the first puller wire is fixedly mounted to the core such that longitudinal movement of the piston and catheter body relative to the core causes longitudinal movement of the first puller wire relative to the catheter body,
   and wherein the second puller wire is anchored to the cam receiver such that rotation of the cam causes longitudinal movement of the cam receiver and second puller wire relative to the piston and catheter body.

16. A catheter according to claim 15, wherein the cam has a ramped proximal end.

17. A catheter according to claim 16, wherein the cam receiver is generally tubular and is mounted in surrounding relation to the core.

18. A catheter according to claim 17, wherein the cam receiver has a distal end with a tab extending distally therefrom, wherein the tab contacts the ramped proximal end of the cam.

19. A catheter according to claim 18, wherein the ramped proximal end of the cam has a tab extending proximally therefrom, such that, when the cam is rotated relative to the piston and core, the tab on the cam contacts the tab on the cam receiver to thereby limit the ability of the cam to rotate.

20. A catheter according to claim 15, wherein the second puller wire is anchored to the cam receiver by being anchored to a puller wire adjuster that is adjustably mounted to the cam receiver such that the longitudinal position of the puller wire adjuster relative to the cam can be altered.

21. A catheter according to claim 20, wherein the puller wire adjuster has one or more teeth extending outward therefrom in a direction generally perpendicular to the axis of the handle and is mounted within a slot in the cam receiver, the slot containing one or more notches that mate with the teeth.

22. A catheter according to claim 15, further comprising a puller wire adjuster mounted within the core at a position proximal to the position where the first puller wire is anchored, wherein the longitudinal position of the puller wire adjuster relative to the core can be altered, the puller wire adjuster comprising an opening extending therethrough in a direction generally transverse to the axis of the handle, such that the first puller wire extends through the core, passes through the opening of the puller wire adjuster and reverses directions.

23. A catheter according to claim 15, wherein the first puller wire has its distal end anchored at or near the distal end of the catheter body.

24. A catheter according to claim 15, further comprising a mapping assembly at the distal end of the catheter body, the mapping assembly comprising:
  a tubular structure comprising a pre-formed generally circular main region generally transverse and distal to the catheter body and having an outer circumference, wherein the tubular structure comprises a non-conductive cover over at least the main region of the mapping assembly, and
  a plurality of electrodes carried by the generally circular main region of the mapping assembly;
  wherein the second puller wire has a distal end anchored in the non-conductive cover for contracting the generally circular main region.

25. A catheter according to claim 24, wherein the first puller wire has its distal end anchored at or near the distal end of the catheter.

* * * * *

UNITED STATES PATENT AND TRADEMARK OFFICE
CERTIFICATE OF CORRECTION

PATENT NO. : 7,274,957 B2 Page 1 of 1
APPLICATION NO. : 11/322582
DATED : September 25, 2007
INVENTOR(S) : Darrell Drysen It is certified that error appears in the above-identified patent and that said Letters Patent is hereby corrected as shown below:

In the Claims

Column 13, line 18, Claim 9    Delete "thereth rough",
                               Insert --therethrough--

Signed and Sealed this

Nineteenth Day of August, 2008

JON W. DUDAS
*Director of the United States Patent and Trademark Office*